(12) United States Patent
Liu

(10) Patent No.: US 6,204,025 B1
(45) Date of Patent: Mar. 20, 2001

(54) EFFICIENT LINKING OF NUCLEIC ACID SEGMENTS

(75) Inventor: Qiang Liu, Arcadia, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/161,466

(22) Filed: Sep. 28, 1998

Related U.S. Application Data

(60) Provisional application No. 60/060,319, filed on Sep. 29, 1997.

(51) Int. Cl.[7] .................................................. C12P 19/34
(52) U.S. Cl. ................... 435/91.1; 435/91.2; 435/69.1; 435/69.7; 435/6; 935/77; 935/78; 935/16
(58) Field of Search .................. 435/91.2, 6, 69.1, 435/69.7; 935/77, 78, 16

(56) References Cited

U.S. PATENT DOCUMENTS

| 5,023,171 | 6/1991 | Ho et al. |
| 5,556,772 | * 9/1996 | Sorge et al. ............... 435/91.2 |
| 5,876,940 | * 3/1999 | Groden et al. ............... 435/6 |

FOREIGN PATENT DOCUMENTS

| 9207075 | 4/1992 | (WO). |
| 9516028 | 6/1995 | (WO). |

OTHER PUBLICATIONS

Liu, Q., "Linking PCR splices small exons into a large DNA molecule amenable to rapid mutation screening" *American J. Human Genetics*, vol. 61, No. 4, Oct. 1997, p. a223.

* cited by examiner

Primary Examiner—Kenneth R. Horlick
Assistant Examiner—Janell E. Taylor
(74) Attorney, Agent, or Firm—Rothwell, Figg, Ernst & Manbeck

(57) ABSTRACT

Gene segment linking provides a simple, cost-effective way to produce an amplified DNA sequence containing linked segments of a single gene or multiple genes. The inventive method involves Multiplex PCR amplifications of gene sequences and linkage of the exons in a single reaction. Multiplex PCR of the gene segments is performed with primers having complementary tails which permit linkage of the gene segments and amplification of the linked gene in one polymerase chain reaction. The ability to construct an amplified DNA from genomic DNA containing several introns in two PCR steps allows the rapid production of DNA which heretofore required many time-consuming and expensive steps.

54 Claims, 9 Drawing Sheets

ID SEGMENTS

CROSS REFERENCE TO RELATED APPLICATION

This application is based on provisional application Serial No. 60/060319, filed Sep. 29, 1997, and applicants claim the benefit of this filing date.

BACKGROUND OF THE INVENTION

1. Technical Field

This invention relates to a method for the efficient amplification of target DNA segments which is particularly advantageous for those target genes containing many small exons. Specifically, the method involves a rapid polymerase chain reaction technique for linking multiple gene segments from a single gene or multiple genes into a large DNA molecule suitable for further analysis.

2. Description of the Background Art

The technique known as the polymerase chain reaction (PCR) is a method of amplification of genomic DNA (Saiki et al., Science: 1350–1354 (1985)). Typically, the method uses two oligonucleotide primers to amplify a single DNA segment millions of times. Each cycle of DNA replication from the original primer(s) produces a product which serves as a template for further primer-dependent replication. This feature of the method results in exponential increases in the desired DNA product with each round of amplification, and a rapid accumulation of DNA. Now an automated technique performed using a thermal cycler and thermostable DNA polymerases, PCR is widely used by molecular biologists to prepare large amounts of synthetic DNA.

This revolutionary technique has been used in a wide variety of fields in molecular biology, and has made possible the rapid identification of disease-associated genes. Using the PCR, it has become feasible to diagnose inherited disorders and susceptibility to disease at the molecular level. Nevertheless, several disadvantages and limitations are recognized in the technique and its application to certain genes.

Customarily, when using PCR to amplify genomic DNA, each gene segment is amplified separately and then analyzed. When the gene of interest contains more than one exon, each exon must be amplified individually using a separate PCR, and then linked together to form a long DNA molecule representing the entire gene (Ho, et al., 1989; Horton, et al., 1989). Because no more than two gene segments can be linked together in each joining PCR, the more exons the gene of interest contains, the more separate amplifications must be individually performed and the more PCRs are needed to link the segments together. For genes which contain a lot of small exons, the preparation of a single gene for analysis can become prohibitively labor-intensive, and require a great deal of time, particularly when the small target exons must be individually scanned for mutations or polymorphisms.

It has been shown that simultaneous amplification of more than one DNA segment can be achieved with a Multiplex PCR using primers tagged with an unrelated 20 nucleotide sequence from bacteriophage M13mp18 (Shuber et al., 1995). However, with this method, products amplified with primers lacking the 20 nucleotide sequence were not reliably produced due to differences in hybridization kinetics among the primers. Using the prior art method, therefore, tagging each primer with an identical 20 nucleotide sequence is necessary to achieve efficient amplification of multiple sequences. This prior art method thus allows multiple amplifications, but the products of the amplification all contain identical unrelated sequences which would have to be removed or extended before they could be linked to form one, long DNA molecule containing all portions of the gene of interest.

After the individual gene segments have been separately amplified, further independent steps are needed to reconstruct the complete desired gene sequence from the smaller segments, with or without an introduced mutation, before the entire gene is ready for analysis. Prior art methods for linking sections of DNA using PCR involve the joining of two segments at a time, each PCR followed by a purification step. (Ho et al., 1989; Kim et al., 1996). The joining of several gene segments together, therefore, requires multiple PCRs and multiple purification steps. For example, joining four exons to form one complete gene using these prior art methods would require four separate amplifying PCRs, four separate purifications of the products and three joining PCRs. Each additional DNA segment in the gene would require an additional PCR to link it to the others, increasing both the time and expense of preparing the DNA for analysis using prior art methods.

In summary, the prior art methods of producing an amplified copy of an entire gene composed of multiple linked exons or an amplified copy of a long DNA molecule composed of gene segments from more than one gene have the disadvantage that multiple PCRs are generally required at each step. Previously, it has not been possible to efficiently amplify multiple gene segments in a single PCR to yield products that had complementary ends suitable for easy, rapid linkage in a second single PCR.

Consequently, there has been a need in the field for a simple and rapid method allowing amplification of DNA which contains several linked DNA segments which occur in non-adjacent portions of target DNA. There is a need for a method which can produce an amplified DNA molecule containing an entire gene of linked exons from genomic DNA, e.g., for DNA diagnosis.

SUMMARY OF THE INVENTION

The present invention provides a method of linking by PCR DNA segments which occur in non-adjacent portions of target DNA wherein each DNA segment contains a sequence complementary to a sequence in the DNA segment or segments to which it is to be linked, comprising using a) a first primer which is complementary to the antisense strand of the first DNA segment to be linked and a second primer which is complementary to the sense strand of the last DNA segment to be linked; and b) at least one polymerase lacking 3'→5' exonuclease activity and at least one polymerase containing 3'→5' exonuclease activity.

In addition, the present invention provides a method of producing and amplifying DNA containing at least three linked DNA segments which occur in non-adjacent portions of target DNA, comprising a) providing a first primer and a second primer for each DNA segment to be amplified, i) the first primer (termed the D primer) having a 3' portion which is complementary to the 3' end of the antisense strand of the DNA segment and a 5' tail which is complementary to the 5' end of the second primer for the previous DNA segment or to a sequence internal to the previous DNA segment; ii) the second primer (termed the U primer) having a 3' portion which is complementary to the 3' end of the sense strand of the DNA segment and a 5' tail which is complementary to the 5' end of the first primer for the subsequent segment or to a sequence internal to the subsequent DNA segment; b) amplifying the at least three DNA segments by multiplex PCR using the pairs of first and second primers; and c) subjecting the at least three amplified DNA segments to a linking PCR using a sense primer which is complementary to the antisense strand of the first segment to be linked and an antisense primer which is complementary to the sense strand of the last segment to be linked.

BRIEF DESCRIPTION OF THE DRAWINGS

FIG. 3 demonstrates the effect of differing amounts of DNA template on the yield of PCR product.

DETAILED DESCRIPTION OF THE PREFERRED EMBODIMENTS

The gene amplification method of the present invention can produce large amounts of DNA composed of several exons or a DNA composed of several non-contiguous DNA segments from the same gene or different genes, without requiring the time-consuming amplification of each separate gene segment. Another advantage of the present invention is the easy, one-step linkage of the gene segments and amplification of the linked product.

The invention has multiple uses which include but are not limited to, the following: i) efficient scanning of mutations by methods such as restriction endonuclease fingerprinting when genomic DNA is analyzed from genes in which there are multiple short exons separated by long introns; ii) joining of different protein domains to generate a recombinant gene/RNA which has novel properties; and iii) linking RNAs together by generating cDNA, linking the cDNA with the primer that contains an RNA promoter sequence, and after linkage transcribing the linked segment to generate the RNA.

Multiplex PCR

Figure 1A:
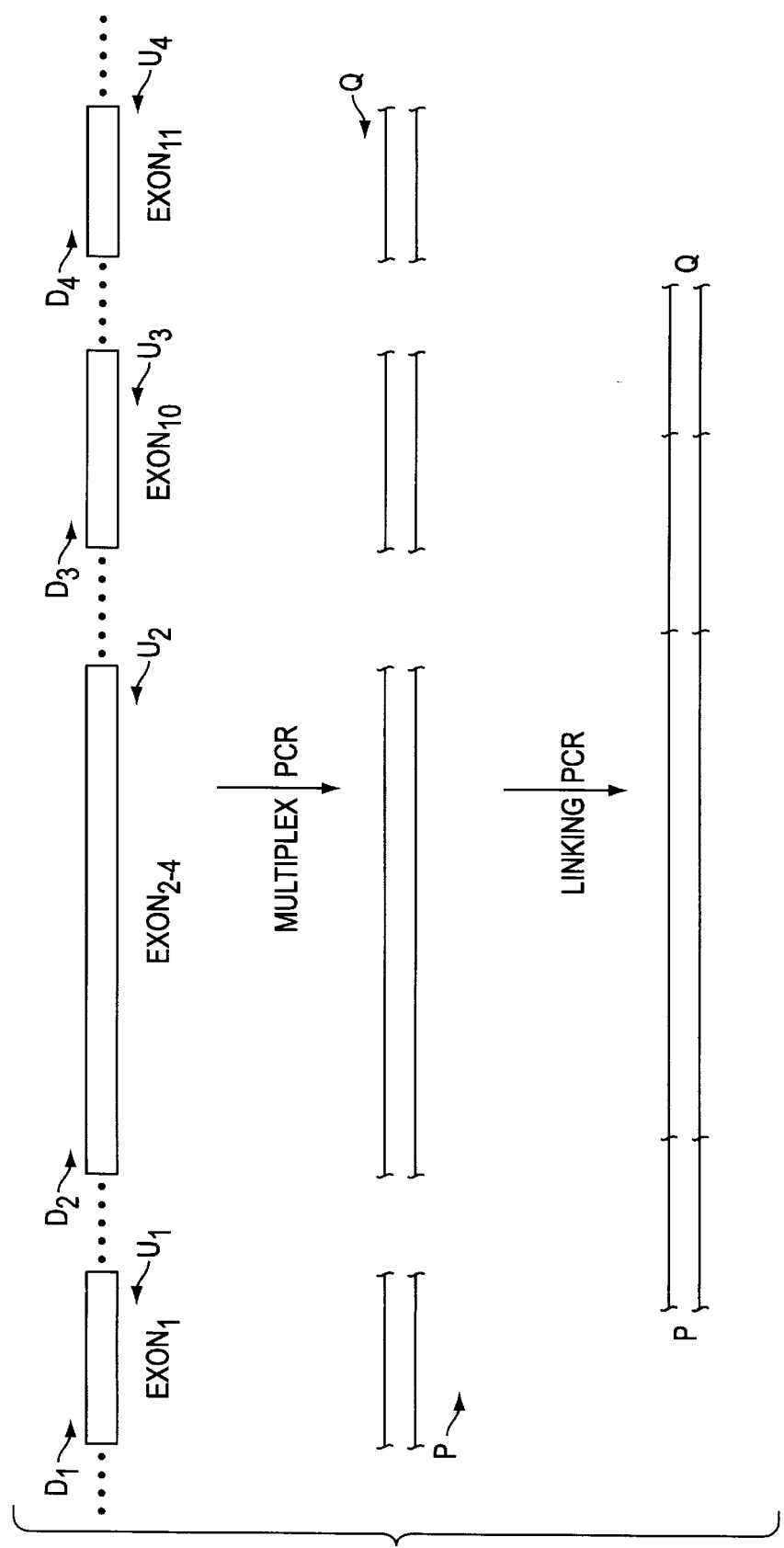
FIG. 1A is a schematic representation of the Multiplex and Linking PCR steps of the inventive process. Four regions of the p53 gene were amplified by Multiplex PCR with the four primer pairs $D_1/U_1$, $D_2/U_2$, $D_3/U_3$ and $D_4/U_4$. Each primer contains a GC-rich tail and a sequence-specific region. The tail of a U primer is complementary to the tail of subsequent D primer. After a simple purification step, the four PCR amplified DNAs ($D_1U_1$, $D_2U_2$, $D_3U_3$ and $D_4U_4$) are linked and amplified by nested P and Q primers.
Figure 1B:
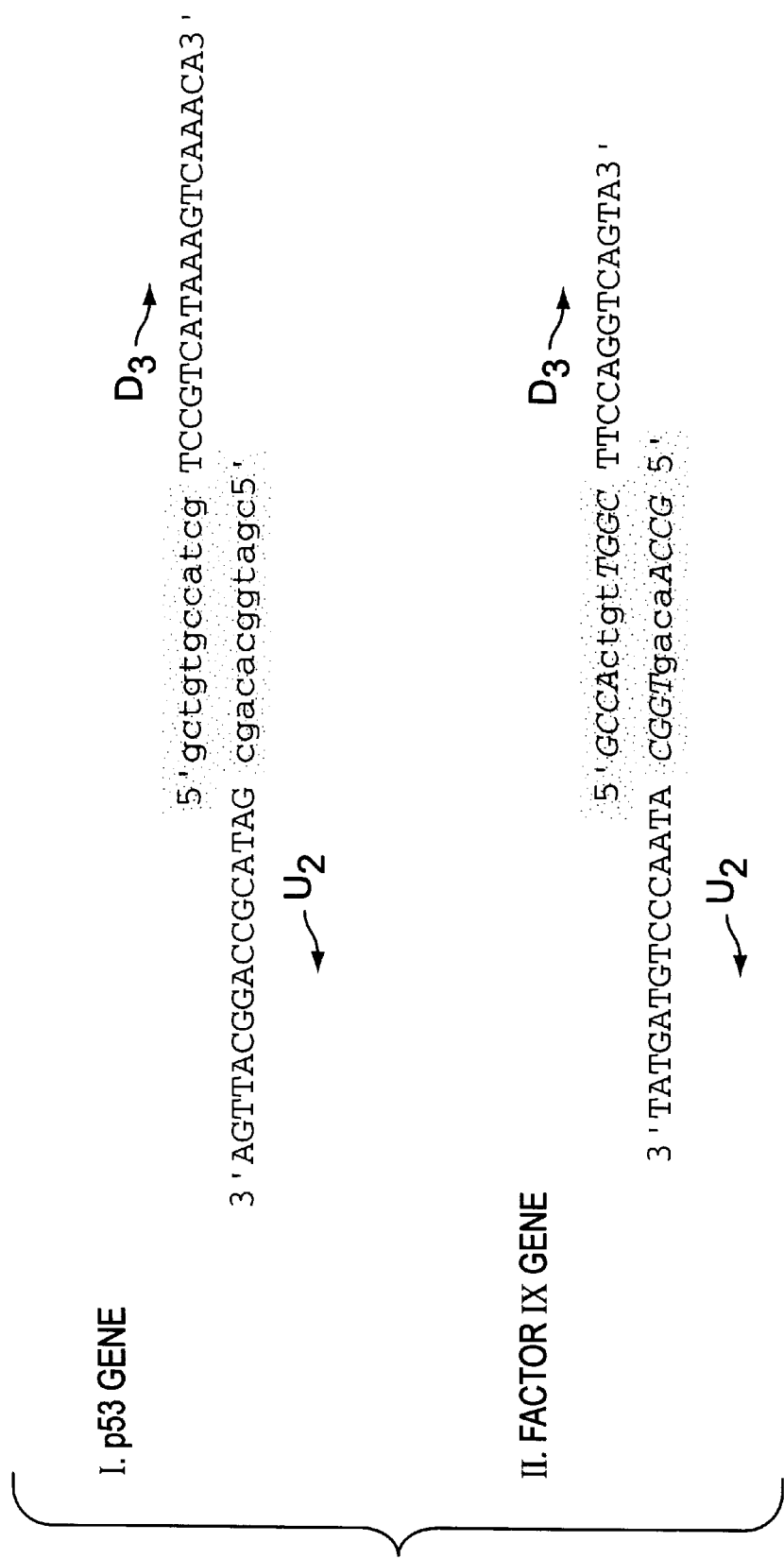
FIG. 1B provides an example showing two types of tails which can be used with the inventive process. The type I tail of $D_3$ primers is not overlapped with the sequence-specific region of $U_2$ primer, while the Type II tail is overlapped by 4 bases. Sense (SEQ ID NO:21) and antisense (SEQ ID NO:22) sequences of the p53 gene, and sense (SEQ ID NO:23) and antisense (SEQ ID NO:24) sequences of the F9 gene are included in the tail.
Figure 1C:
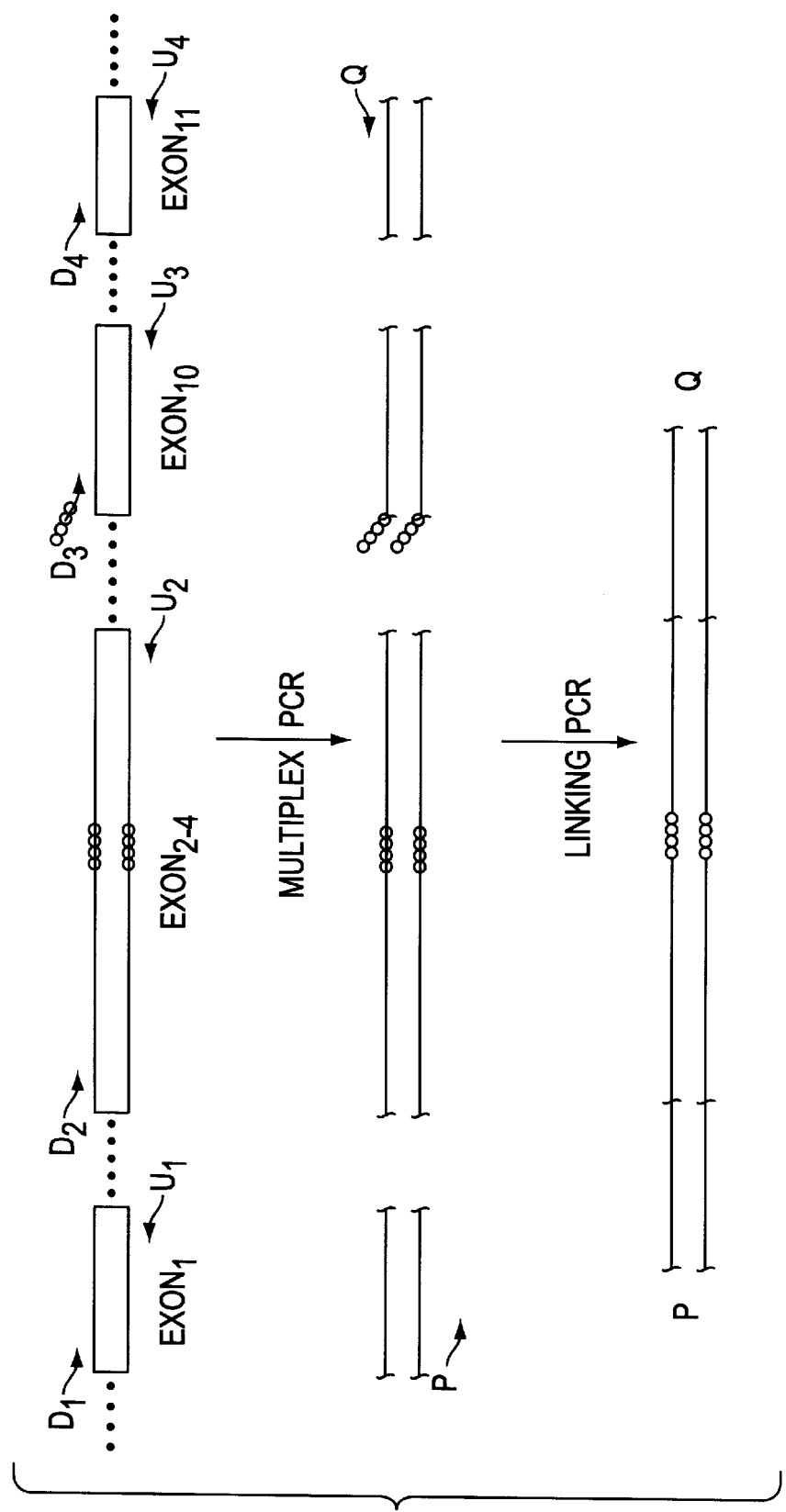
FIG. 1C. This schematic diagram illustrates the use of the type III tail, in which the tail sequence is complementary to an internal portion of the DNA sequence to be joined.

Multiplex PCR is the amplification of the desired regions (for example, exons) of the genetic material using a pair of primers for each individual region. FIG. 1 illustrates in schematic form the amplification of four exons simultaneously with four primer pairs prior to the linking-step. The primer pairs are designated $D_1/U_1$, $D_2/U_2$ ... $D_n/U_n$. Each primer contains a GC-rich tail and a sequence-specific region, and the tail of each U primer is complementary to the tail of the subsequent D primer. Three types of primer tails are contemplated for use with the invention. In type I primers the tail of the D primer does not overlap with the sequence-specific region of the previous U primer. In type II primers, the tail of the D primer overlaps the sequence-specific region adjacent to the previous U primer. See FIG. 1B. Type III primers contain a tail portion which is complementary to a sequence internal to the previous gene segment. See FIG. 1C for an example in schematic form.

Primers were designed with Oligo 5 software (National Biosciences, Inc.) and the GCG program (Genetic Computer Group, Inc.). Oligo 5 calculates primers' melting temperature ($T_m$) by the nearest neighbor method at 50 mM KCl and 250 pM DNA. the $T_m$ value of each PCR DNA was estimated by the Wetmur formula ($T_m^{product}$=81.5+16.6 log [$K^+$]+0.41(%G+%C)−675/length (Wetmur, 1991). Type I tails do not overlap the sequence-specific region of the complementary primer, while type II tails overlap the sequence-specific region for four bases. Tails which overlap by more or fewer bases are also suitable for use with the invention. Type III tails are complementary to an internal sequence within the previous gene segment.

Guidelines for Primer Design

Designing the appropriate primers is a critical step in successfully performing Linking PCR. Based on this work, building on other studies using Multiplex PCR (Liu et al. 1997), the following guidelines for primer design were developed and successfully applied.

a. Sequence-specific region

The sequence-specific region affects the yields and specificities of the Multiplex PCR. The criteria are set as follows:

1. The $T_m$ value should be approximately 35° C. below the average $T_m$ value of the targeted regions. A $T_m$ value lower than this may result in low PCR yields, especially if the region of the gene segment to be amplified contains a high GC percentage.

2. The stringency for dimer or hairpin formation at the 3' end should preferably be set at ≦4 base pairs among all primers. This has the potential to cause a greater problem in Multiplex PCR than in ordinary PCRs using only two primers.

3. The stringency for false priming sites at the 3' end should preferably be set at ≦6 base pairs for all strands and for all regions.

4. Internal stability may be chosen based on the instructions in the Oligo 5 software package.

b. Tail region

The tail is short (preferably less than 20 bases) and contains a high percentage of GC bases, which functions to provide consistent and balanced high yields of Multiplex PCR products, and an efficient and specific "linker" for the Linking PCR. The criteria should be set as follows:

1. The GC content should preferably be from 60% to 70%.

2. The tail size is preferably 10–15 bases long and most preferably 12 bases long.

3. The stringency for false priming of the primer's antisense sequence at its 3' end should preferably be ≦6 bases for any strand and any target.

4. A type II tail is preferred.

Optimization of Multiplex PCR

The parameters of the PCR may be optimized according to Shuber, et al. (Shuber et al., 1995) or determined empirically. For the following examples, the optimization strategy of Shuber, et al. (Shuber et al., 1995) was followed, except for the annealing temperature. The optimal annealing temperature was determined empirically and was expected to be approximately 20–25° C. below the average $T_m$ of the gene regions being amplified. (Liu et al., 1997). A preferred strategy for optimization of the Multiplex PCR step is as follows:

a. Test each PCR:

Concentrations of primer, Mg, DMSO, and the amount of TaqGold DNA polymerase should be optimized for each polymerase chain reaction. The optimal annealing temperature should be approximately 20–25° C. lower than the average $T_m$ of the regions to be amplified, but ultimately should be determined empirically. If a region is not being efficiently amplified, adding an additional one or two bases to the sequence-specific region of the primer may increase the yield.

b. Test the Multiplex PCR:

The common parameters of each PCR should be chosen to generate balanced high yields of the specific desired Multiplex PCR products. The Taq DNA polymerase may be present in amounts as high as 2–6 units per 25 $\mu$l reaction. Rarely, the primer concentration may need further adjustment to achieve even, balanced yields of each DNA segment. If satisfactory results are still not achieved, a change in the primer sequence may be necessary.

TaqGold with hot-start was found important to prevent primer dimer formation and false priming. One potential difficulty in the p53 gene was the amplifications of exons 10 and 11, which are separated by an intron of 800 base pairs. However our results showed no large PCR DNA spanning the two exons when the $T_m$ of the sequence-specific regions of the $U_3$ and $D_4$ primers was increased and their relative concentrations adjusted according to our preferred optimization scheme.

Linking PCR

Amplified DNA segments produced by multiplex PCR or any other suitable method may be joined with the linking PCR method, with our without prior purification to remove unincorporated primers. First, the antisense strands of $U_1$ and $D_2$ tails, $U_2$ and $D_3$ tails, and $U_3$ and $D_4$ tails are annealed and extended, so the four $D_1U_1$, $D_2U_2$, $D_3U_3$, and $D_4U_4$ DNAs are linked into a $D_1U_4$ molecule in numerical order. If the primers are complementary to a different region of the DNA segment to be joined, the complementary regions are annealed and extended. Second, PCR amplifies the joined template with nested primers such as P and Q. (FIG. 1A).

Tails of 12-base size worked efficiently, although tails of 10–15 bases, or a greater range, are also suitable. The tails of primers P and Q prevent "megapriming," which occurs when a PQ product generated in an earlier cycle acts as a primer for a larger $D_1U_4$ template in a subsequent cycle (Sarkar and Sommer, 1992; Sarkar and Sommer, 1990). Also, the tail acts as a switch from low amplification efficiency to high efficiency, depending on which template of $D_1U_4$ or PQ to which the primer anneals (Liu, et al. 1997).

One of three DNA polymerases lacking 3'→5' exonuclease activity (Tth, Taq (Boehringer Mannheim) and Tfl (Promega)) were combined with one of two enzymes possessing 3'→5' exonuclease activity (Vent (New England BioLabs), Pfu (Stratagene)) to perform the inventive method. The effect of the enzyme which lacks 3'→5' exonuclease activity is speculated to remove the potential extra non-template A base at the 3' end of the PCR product (Wu et al., 1989). Persons of skill in the art will recognize that other enzymes may be used with the present invention, such as Pwo and Plo, but it is key that the polymerase activity is due to one (or more) enzymes without 3'→5' exonuclease activity and one (or more) enzymes with 3'→5' exonuclease activity. These enzymes and enzyme combinations serve only as examples by way of illustration and are not intended to limit the invention.

A solid or liquid macromolecular additive may be used in the linking PCR mixture. Macromolecular additives such as polyethylene glycol (PEG) may reduce the amount of template needed to obtain a satisfactory result.

Optimization of Linking PCR

The following preferred parameters are not intended to limit the invention. Skilled molecular biologists will recognize that different parameters may be used with the invention.

a. Primers

The nested primers P and Q should be designed using the same criteria and methods as described above for the D and U primers, except that the $T_m$ of the sequence-specific regions are preferably approximately 35–40° C. lower than the $D_1U_4$ DNA product.

b. Polymerases

Tth/Vent DNA polymerases are preferably present at approximately 1U/0.1U or 1U/0.05U per 25 µl reaction.

c. Linkage efficiency

The linkage of individual DNA segments is preferably tested by measuring the linking efficiencies of all the regions desired to be linked, and all shorter linked segments. For example, if the desired complete DNA sequence is made up of 4 segments, the linkage efficiency of 4, 3, and 2 segments would be measured with the appropriate primer pairs. Table 1 illustrates this suggested method.

f. Cycle number

The optimal cycle number for each Linking PCR should be determined. Routinely, 20–25 cycles are most efficient and yield the best product.

g. Quality control

The identity and quality of the Linking PCR product is preferably confirmed by direct sequencing. If the product is not of the correct sequence, the tails of the primers from the multiplex step and the P and Q primers should be double-checked.

EXAMPLES

1. Multiplex PCR of p53 Gene Exons

Each of four primer pairs of $D_1/U_1$, $D_2/U_2$, $D_3/U_3$, and $D_4/U_4$ (Table 1A) were used to amplify exons 1, 2–4, 10 and 11 in the p53 gene. Each primer contained a GC-rich tail and a sequence-specific region. The tails of the U primers were complementary to the tails of each subsequent D primer. This example used a type I tail, in which the tail of the $D_3$ primer is not overlapped with the sequence-specific region of the $U_2$ primer. (Table 1A, FIG. 1A). A hot-start at 92° C. for 10 minutes was included for enzyme activation. The denaturation was at 94° C. for 15 seconds, and the annealing was at 55° C. for 30 seconds, followed by elongation at 72° C. for 2 minutes, for a total of 35 cycles with a Perkin Elmer model 9600 thermal cycler. The PCR mixture contained 50 mM KCl, 10 mM Tris/HCl, pH 8.3, 1.5 mM MgCl$_2$, 200 µM of each dNTP, 5% DMSO, 3–4U of TaqGold DNA polymerase (Perkin Elmer), and 250 ng of genomic DNA per 25 µl of reaction. After purification in a Centricon®-100 microconcentrator (Amicon), the amount of DNA was determined by spectrophotometer at 260 nm. The four expected DNA products were obtained in similar molecular ratio, and the complementary tails did not cause obvious problems.

TABLE 1

Relative mole ratios of PCR products with different primer pairs

| Gene | Template amount | $D_1/U_2$ | $D_2/U_3$ | $D_3/U_4$ | $D_1/U_3$ | $D_2/U_4$ | $D_1/U_4$ | P/Q | None |
|---|---|---|---|---|---|---|---|---|---|
| p53 | 40 ng | 10.85 | 8.10 | 9.09 | 6.73 | 7.27 | 4.81 | 5.31 | 0.22 |
|  | 20 ng | 7.74 | 4.56 | 7.60 | 0.98 | 3.19 | 0.57 | 1.00 | 0.17 |
|  | 10 ng | 8.54 | 4.44 | 7.08 | 1.07 | 0.56 | 0.09 | 0.13 | 0 |
| F9 | 40 ng | 18.54 | 18.58 | 17.60 | 14.43 | 14.27 | 8.77 | 4.87 | 0.16 |
|  | 10 ng | 17.78 | 17.60 | 16.85 | 8.18 | 8.58 | 3.61 | 1.00 | 0 |

The mole ratio of $D_1U_2$, $D_2U_3$, $D_3U_4$, $D_1U_3$, $D_2U_3$ and no primer to $D_1U_4$ primer is obtained by normalizing the relative yield by the potential amount of incorporated radioactive $^{32}$P-dCTP.

d. Annealing temperature

Figure 5:
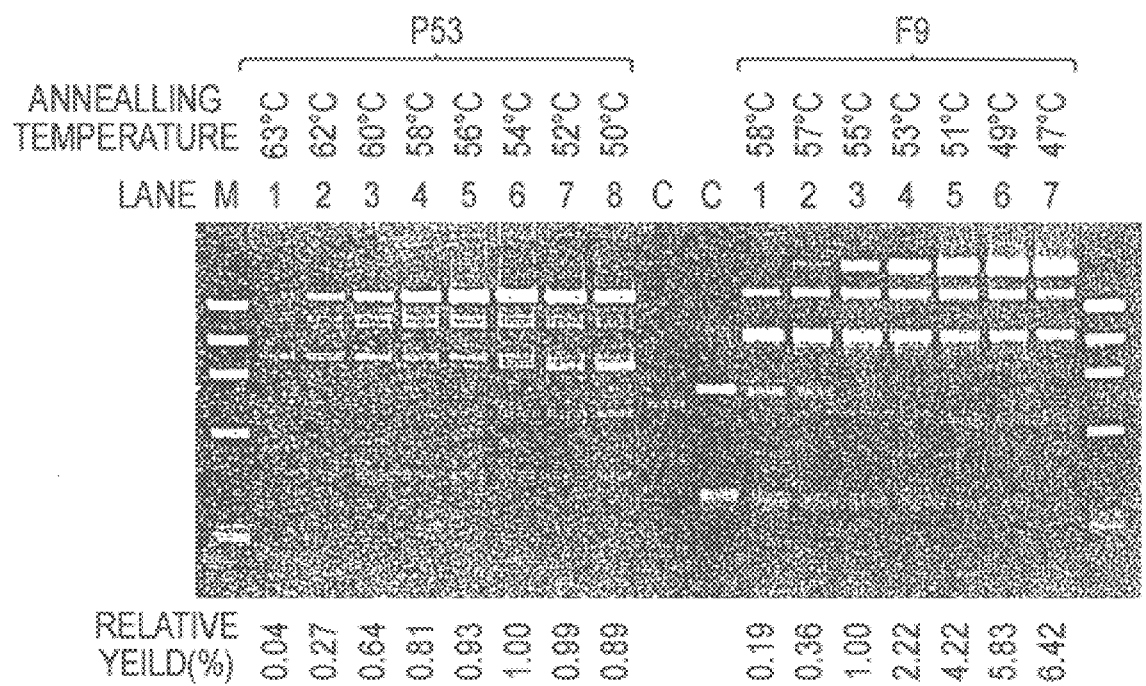
FIG. 5 gives the relative yields of PCR products of the p53 and F9 genes with different annealing temperature.

The optimal annealing temperature should be determined using a large amount of DNA templates, and is generally associated with the percentage of GC bases in the DNA templates. See FIG. 5.

e. DNA template concentration

Figure 3A:
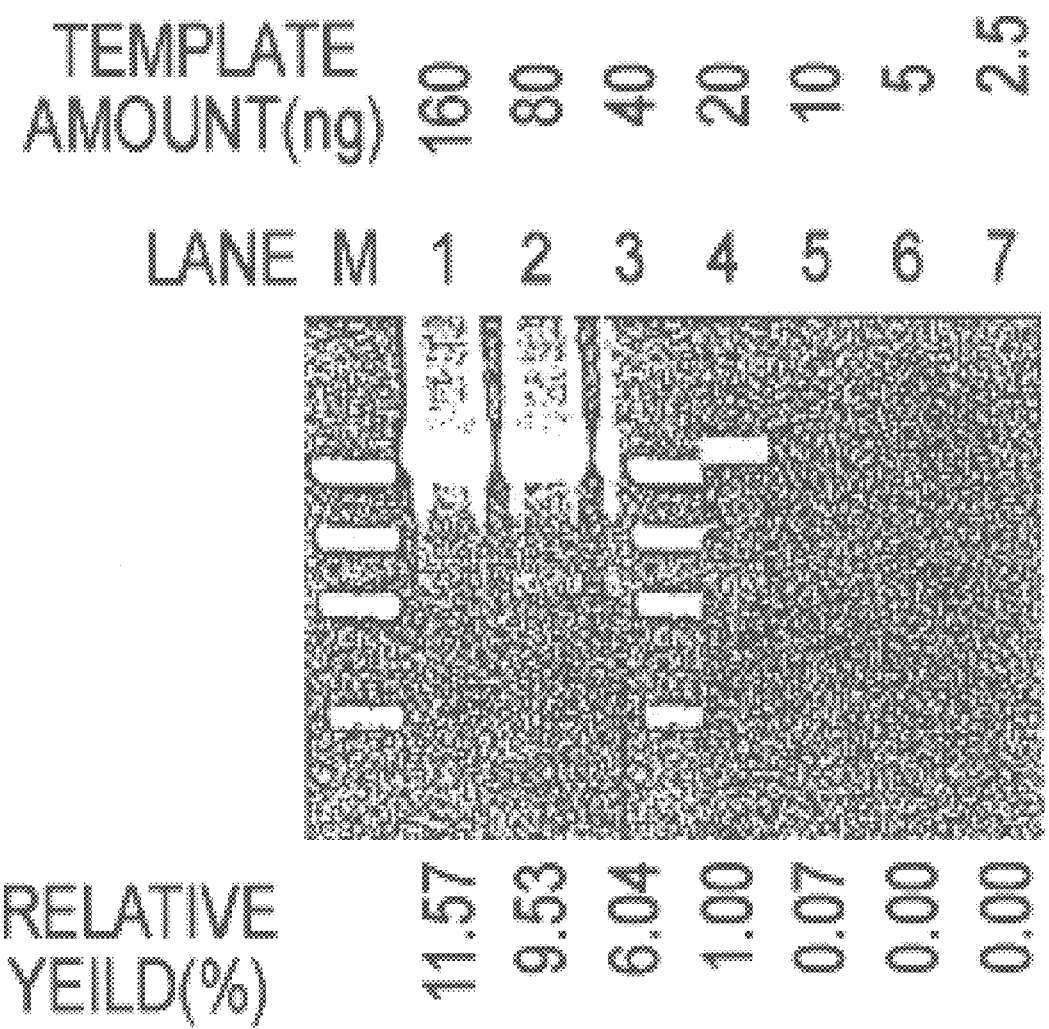
In FIG. 3A, the p53 gene was amplified using Tth/Vent DNA polymerases. Tth/Vent DNA polymerases were applied with increasing amounts of template DNA and the p53 PQ product quanti- tated.

The preferred DNA template concentration is determined as shown in FIG. 3, and is dependent on how many DNA segments are to be linked together.

2. Multiplex PCR of F9 Gene Exons

Each of four primer pairs of $D_1/U_1$, $D_2/U_2$, $D_3/U_3$, and $D_4/U_4$ (Table 1B) were used to amplify exons 1, 2–3, 4, and 5 of the F9 gene. As in the above example, each primer contained a GC-rich tail and a sequence-specific region, and the tails of the U primers were complementary to the tails of each subsequent D primer. This example uses a type II tail, in which the tail of the $D_1$, $D_2$, and $D_3$ primers overlapped for four bases the sequence-specific region of the corresponding U primers. (Table 1B, FIG. 1B). The PCR mixture and reaction parameters were the same as in example 1 with the exception that 5% DMSO was omitted from the reaction mixture.

TABLE 1

Primers
A.

| # | Name[a] | Conc. (μM) | Sequence[b] | tT$_m$[c] (° C.) | cT$_m$[c] (° C.) |
|---|---|---|---|---|---|
| p53 1 | (5'UT)(750)28D$_1$ | 0.05 | gttcgcagagggTTTGTGCCAGGAGCCT | 28.9 | 46.1 |
| 2 | (I1)(995)29U$_1$ | 0.05 | aggacgaccgctAGCCCGTGACTCAGAGA | 31.8 | 44.9 |
| 3 | (I1)(11641)30D$_2$ | 0.1 | agcggtcgtcctCTAGGGTTGGAAGTGTCT | 31.8 | 43.3 |
| 4[d] | (I4)(12352)30U$_2$ | 0.1 | cgatggcacagcGATACGGCCAGGCATTGA | 30.9 | 51.5 |
| 5 | (I9)(17480)31D$_3$ | 0.06 | gctgtgccatcgTCCGTCATAAAGTCAAACA | 30.9 | 43.2 |
| 6 | (I10)(17741)31U$_3$ | 0.2 | gaggtgggtgtcCCTATGGCTTTCCAACCTA | 21.6 | 46.9 |
| 7 | (I10)(18547)31D$_4$ | 0.2 | gacacccacctcACCCTCTCACTCATGTGAT | 21.6 | 42.7 |
| 8 | (I11)(18756)29U$_4$ | 0.06 | cccgtgaggacaGACCCAAAACCCAAAAT | 29.2 | 43.9 |
| 9 | (5'UT)(769)29D[P] | 0.05 | caacgggtcaggAGGGGTTGATGGGATT | 29.5 | 43.3 |
| 10 | (I11)(18717)29U[Q] | 0.05 | cgtgtggctgctGAGGGAGGCTGTCAGTG | 29.6 | 44.6 |
| F9 11 | (5'UT)(-102)25D$_1$ | 0.1 | tcgcagagGAGGCCATTGGAAATA | -7.2 | 41.9 |
| 12 | (I1)(248)25U$_1$ | 0.1 | gtaagcggt*CGTG*CTGGCTGTTAGA | 30.7 | 41.8 |
| 13 | (I1)(6104)29D$_2$ | 0.2 | cacgaccgc*TTAC*TGGAATTCTCTTGACT | 30.7 | 40.2 |
| 14 | (I3)(6870)27U$_2$ | 0.2 | gccaacag*TGGC*ATAACCCTGTAGTAT | 29.6 | 41.8 |
| 15 | (I4)(10264)25D$_3$ | 0.14 | gccactgt*TGGC*TTCCAGGTCAGTA | 29.6 | 43.1 |
| 16 | (I4)(10618)28U$_3$ | 0.14 | ggtccggg*ATCA*AAGGTATGTTTTTAAG | 32.3 | 38.5 |
| 17 | (I4)(17584)27D$_4$ | 0.1 | tgatcccg*GACC*CATACATGAGTCAGT | 32.3 | 40.4 |
| 18 | (I5)(17897)27U$_4$ | 0.1 | acggagacAGGAAGCAGATTCAAGTAG | -12.0 | 40.6 |
| 19 | (5'UT)(-57)23D[P] | 0.05 | tcaaggagGAGGGAGATGGACAT | -17.4 | 33.6 |
| 20 | (I5)(17856)23U[Q] | 0.05 | tggtgtgcTTAAAATGCTGAAGT | -17.1 | 27.2 |

[a]p53 gene PCR products are D$_1$U$_1$ (270 bp, 58% G + C), D$_2$U$_2$ (736 bp, 59% G + C), D$_3$U$_3$ (286 bp, 55% G + C), D$_4$U$_4$ (235 bp, 54% G + C) and PQ (1433 bp, 57% G + C). The numbering system is based on GenBank Accession: X54156. F9 gene PCR products are D$_1$U$_1$ (367 bp, 40.6% G + C), D$_2$U$_2$ (784 bp, 31.4% G + C), D$_3$U$_3$ (371 bp, 39.9% G + C), D$_4$U$_4$ (330 bp, 36.4% G + C) and PQ (1702 bp, 35% G + C). The numbering system is as described in Yoshitake, et al. (Yoshitake, et al., 1985). Key to primer names: 5'UT indicates the primer begins at a 5' untranslated region; the letter I followed by a number indicates the primer begins at that intron; the number in parenthesis indicates the nucleotide at which the sequence begins; the following number indicates the sequence length; and the letter D or U indicates a downstream or upstream primer.
[b]The underlined region is the tail and the capitalized region is the sequence-specific region.
[c]tT$_m$ and cT$_m$ represent the T$_m$ values of the tail and the sequence-specific region of a primer, respectively.
[d]The anti-sense sequences of primer #4 have 7 bp false priming sites at the 31 end.

3. Linking PCR

Linking PCR was performed as follows. Denaturation proceeded at 94° C. for 15 seconds, annealing at 55° C. for 30 seconds rammed to 72° C. within one minute, and then elongation at 72° C. for 2–3 minutes, for a total of 15 cycles. The mixture contained 100 mM KCl, 10 mM Tris/HCl, pH 8.9, 1.5 mM MgCl$_2$, 50 μ/ml BSA, 0.05% (v/v) Tween 20, 200 uM of each dNTP, 1U of Tth (Boehringer Mannheim) and 0.1 U of Vent (New England Biolabs) DNA polymerases, 20 ng each of the four DNAs, and 5 μCi of alpha-$^{32}$P-dCTP (300 Ci/mmol, Amershar) per 25 μl reaction; unless mentioned elsewhere. The PCR products were separated on a 2% agarose gel, which was then stained with ethidium bromide and UV photographed with an AlphaImager™ 2000 CCD camera (Alpha Innotech). The PCR was quantitated by PhosphorImager with ImageQuant software (Molecular Dynamics) after the dried gel was exposed for 30 minutes. The PCR yields were quantitated as "random units," i.e. the number of pixels in the PCR band minus the background.

Figure 4:
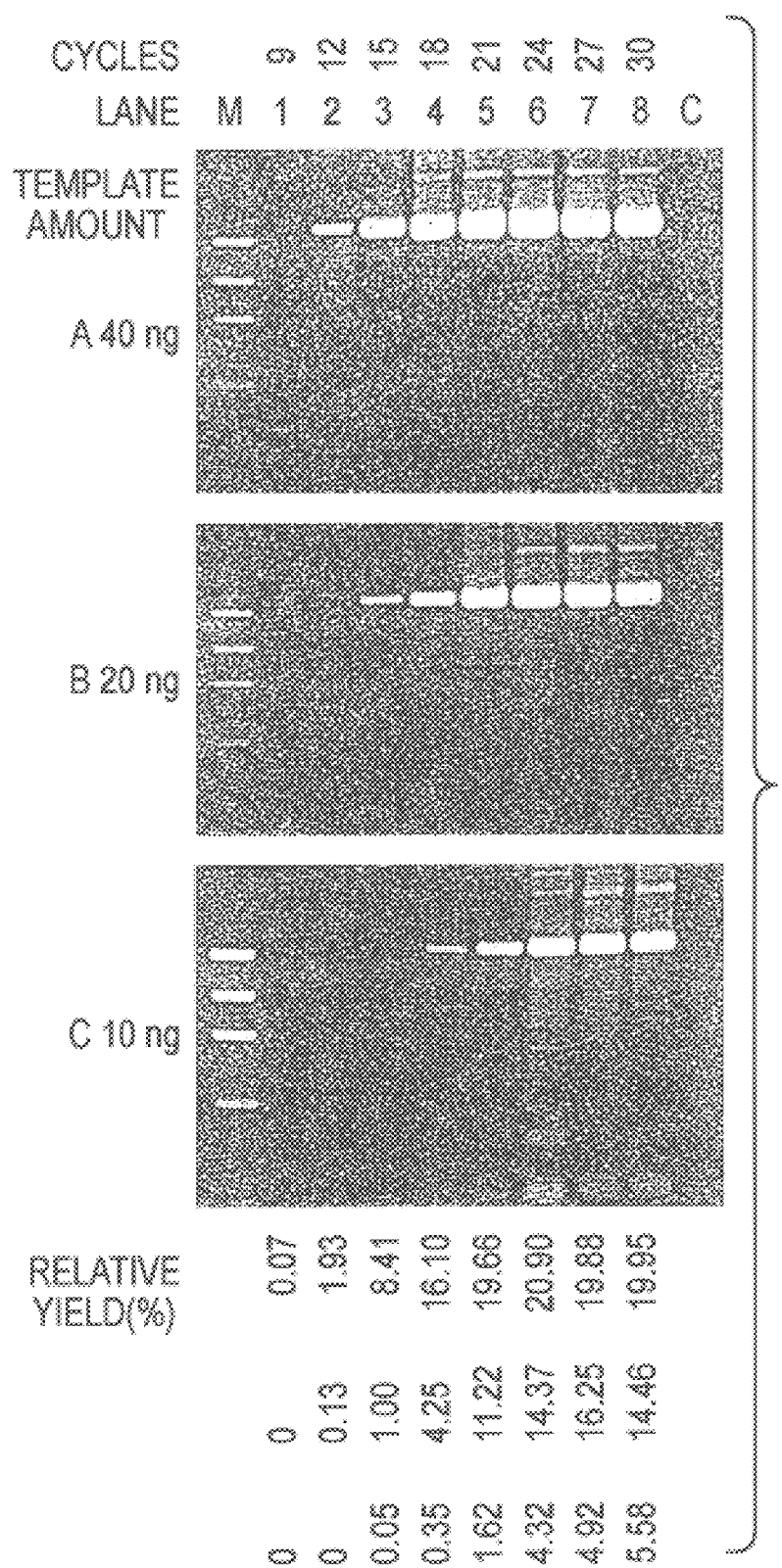
FIG. 4 presents the relative yields and accumulation of PCR product. Aliquots of identical radioactively labeled Linking PCR mixtures were removed from the thermocycler every 3 cycles from 9 to 30 cycles and the PQ PCR product was quantitated. Forty nanograms (4A), 20 ng (4B), or 10 ng (4C) of p53 DNA templates per 25 μl reaction were used.

To quantitate the accumulation of linked PQ PCR product, aliquots of the Linking PCR reaction mixture were removed from the thermocycler every 3 cycles from 9 cycles to 30 cycles. Reactions containing 40 ng, 20 ng, and 10 ng of the four p53 DNA templates per 25 μl reaction volume (FIG. 4) were used. The first appearance of the faint PQ product was dependent on the amount of DNA template in the reaction mixture, supporting the existence of four-component linking kinetics. During the later cycles, the PQ PCR product accumulated to a considerable extent, and reached a saturation point. The point at which saturation was reached was also dependent on the amount of DNA template originally added to the reaction. Furthermore, the relative presence of intermediate products was greatly reduced after 20 cycles (FIG. 4). A similar result was obtained with the F9 gene.

4. Optimization of Linking PCR Parameters a. Enzyme type, concentration, and ratio

Figure 2A:
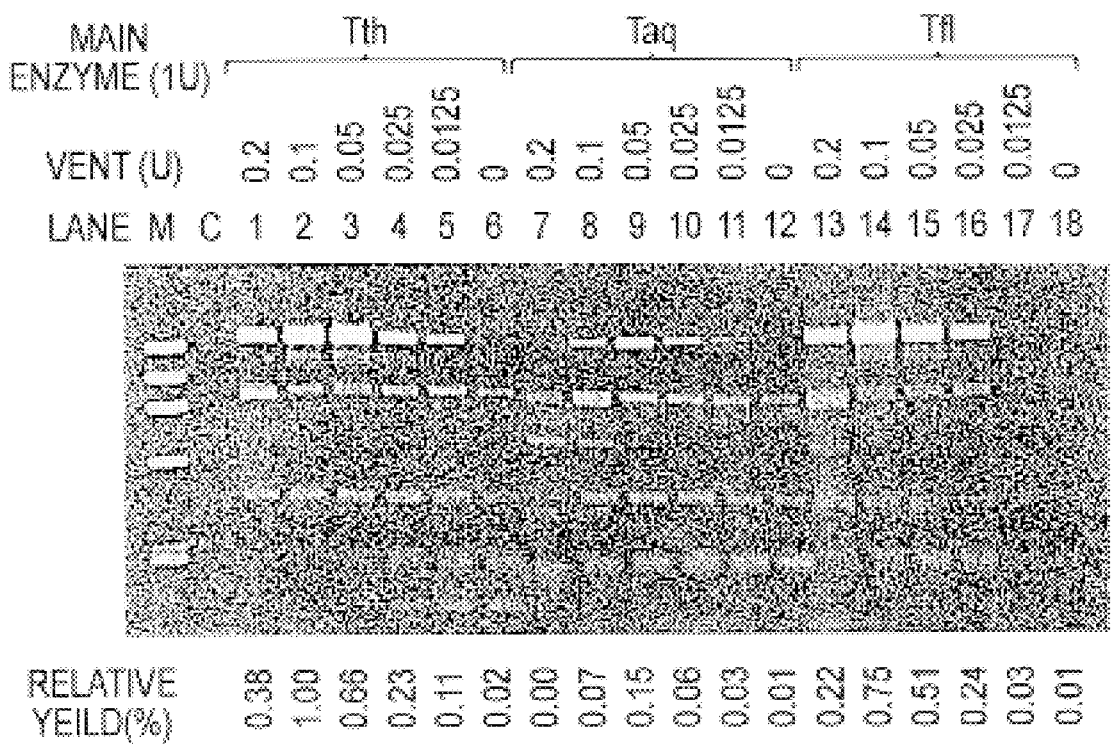
FIG. 2A shows the relative yields of PCR product of the p53 gene with varied amounts of Vent and fixed amounts of Tth, Taq, or Tfl enzymes. Fixed amounts of Tth, Tag, or Tfl and increasing amounts of Vent were used to link and amplify segments of the p53 gene. Relative yields of the linked PQ product were quantitated using a PhosphorImager (Molecular Dynamics) after 15 cycles.

As seen in FIG. 2A, 1U of Tth, Taq, or Tfl was mixed with 0–0.2U Vent to test the yield of p53 gene PCR product as quantitated by PhosphorImager after 15 cycles under various -enzyme conditions. The results show that Tth/Vent in ratios of 1:0.1 and 1:0.05 (lanes 2 and 3) generated the highest yield. Relative linking PCR efficiencies were Tth/Vent or Tfl/Vent>Tfl/Pfu>Taq/Pfu>Tth/Pfu>Taq/Vent. Any single enzyme alone did not work optimally.

Figure 2B:
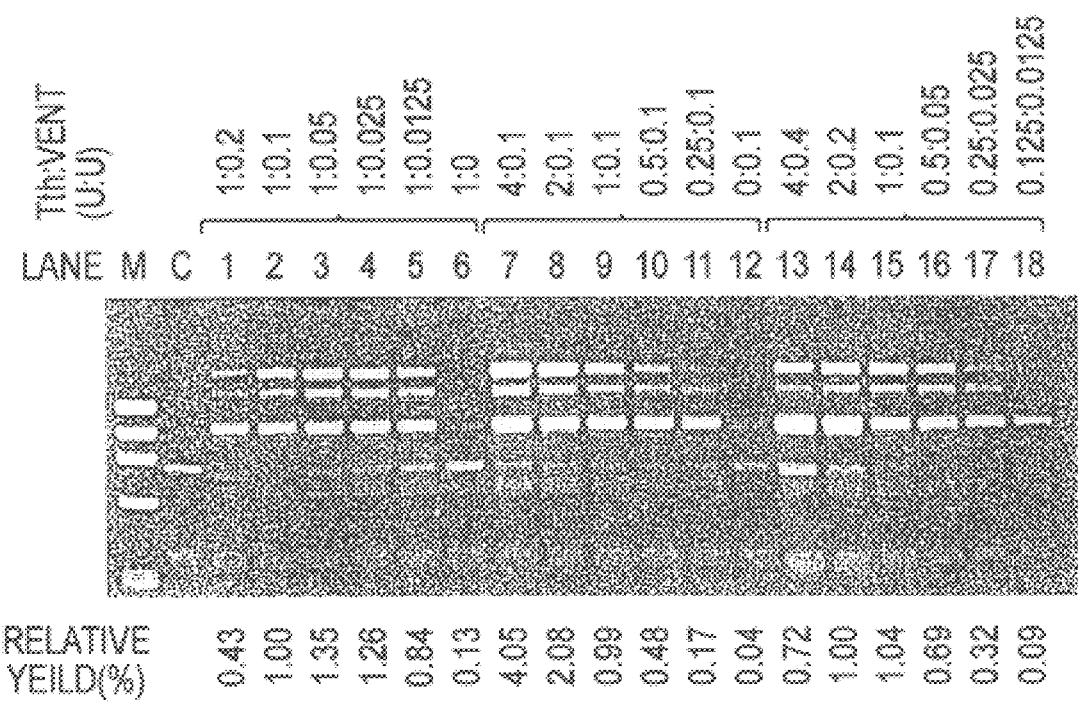
FIG. 2B shows the relative yields of PCR product of the F9 gene with varied ratios of Tth and Vent enzymes. Increasing amounts of Tth and Vent were used to link and amplify segments of the F9 gene. Again, relative yields of the linked PQ product were quantitated using a PhosphorImager after 15 cycles (M=120 ng φx174/Hae III DNA marker).

Further tests with Tth and Vent were performed in linking exons of the F9 gene, changing both the amounts and ratio of the two enzymes in the reaction (FIG. 2B). Amounts of Tth ranged from 0.125U to 4U, and amounts of Vent ranged from 0.0125U to 0.4U, with 4U Tth and 0.1U Vent generating the highest yield (lane 7). The results show that both the absolute amount of the two enzymes and the ratio influence the efficiency of the linking polymerase chain reaction. Similar results were achieved when linking PCR was performed with segments containing 15 base pairs of complementary sequence and when 49 ng of template DNA was used.

b. DNA template concentration

Figure 3B:
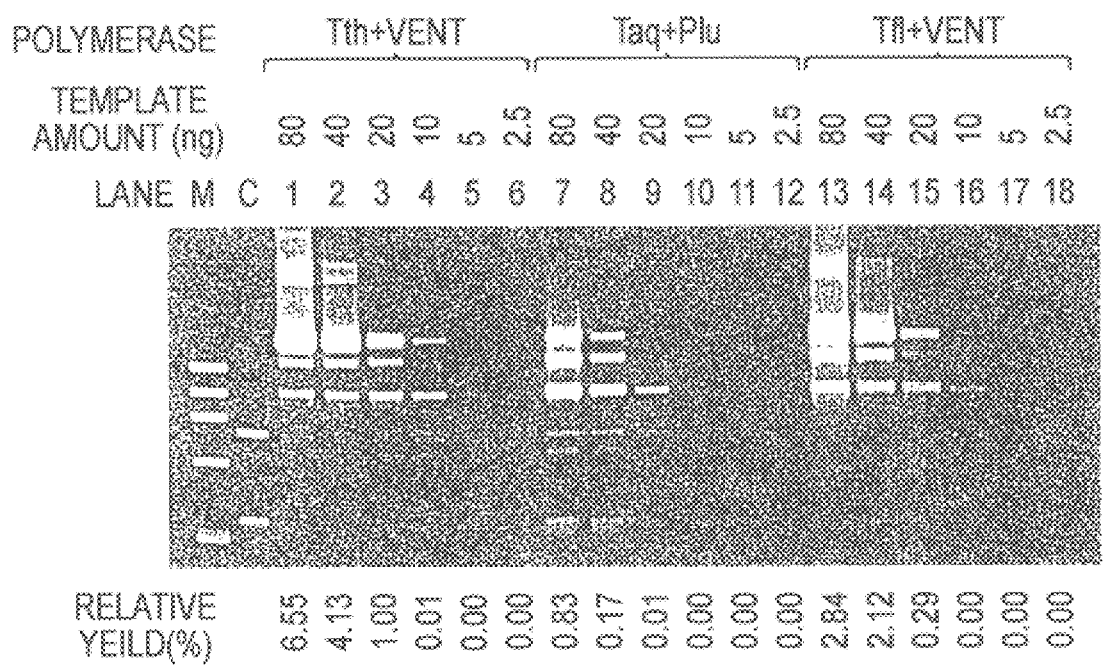
In FIG. 3B, Tth/Vent, Taq/Pfu or Tfl/Vent DNA polymerases were applied to the F9 gene. Tth/vent, Taq/Pfu or Tfl/Vent were applied to the F9 gene.

Using increasing amounts of each of the four DNA templates ($D_1U_1$, $D_2U_2$, $D_3U_3$, and $D_4U_4$) with a constant amount of Tth/Vent, a "threshold" between 10 and 20 ng template DNA per 25 μl reaction volume (lanes 4 and 5) was noted. Doubling the template concentration resulted in a 14–16-fold increase in linked p53 product. The yield of linked product is therefore the template concentration to the fourth power (yield=(total amount of all template)$^4$). This was confirmed by repeating the experiment using separate steps of linking and subsequent amplification. In addition, an experiment using DNA templates with longer 15-base tails produced the same effect. Similar "threshold" effects occurred when Taq/Pfu and Tfl/Vent enzymes were applied to the F9 gene (40% GC content rather than 57% GC content as in the p53 gene), indicating the effect is not dependent on either the enzymes or the particular DNA templates used (FIG. 3B).

c. Linkage with different primer pairs

Besides the primer pairs of P/Q, other primer pairs were compared: $D_1U_2$, $D_2U_3$, and $D_3U_4$ amplified two linked regions; $D_1U_3$ and $D_2U_3$ amplified three linked regions, and $D_1U_4$ amplified four linked templates, respectively. The mole ratio of $D_1U_2$, $D_2U_3$, and $D_3U_4$; of $D_1U_3$ and $D_2U_3$; and of $D_1U_4$ (the normalized relative yield or number of potential incorporated radioactive $^{32}$P-dCTP) reflect the relative linking efficiencies of two-, three-, and four-template reactions. Table 2 shows that Linking PCRs linking two templates are much more efficient than those linking four templates. Also, Linking PCRs linking two templates are much less dependent on the template amount.

d. Tail length

Tails of 10, 12, or 15 bases, designed to contain 60–70% GC, were tested linking exons of the F8 gene. Tails containing 12 bases were most efficient at linkage. Further experiments with 12- and 15-base tails in the p53 gene ($T_m$ ranging from 21.6° C. to 44.1° C.) and 12-base tails in the F9 gene ($T_m$ ranging from 29.6° C. to 32.3° C.) yielded the same results: 12-base tails were most efficient.

e. Annealing temperature

The effects of annealing temperature were studied using a Gradient Robocycler (Stratagene). For the p53 gene, using four templates with 12-base tails, linked product was formed with high yields at annealing temperatures from 50° C. up to 58° C. For the F9 gene, under the same conditions, high yields of linked product were formed at annealing temperatures from 47° C. up to 55° C. The optimal annealing temperature is relatively low and has a broad range. The optimal annealing temperature also is associated with the GC content of the templates.

I claim:

1. A method of linking by PCR at least three DNA segments which occur in non-adjacent portions of target DNA wherein each DNA segment contains a sequence complementary to a sequence in the DNA segment or segments to which it is to be linked, comprising subjecting the at least three DNA segments to a linking PCR using
   a. a first primer which is complementary to the antisense strand of the first DNA segment to be linked and a second primer which is complementary to the sense strand of the last DNA segment to be linked; and
   b. at least one polymerase lacking 3'→5' exonuclease activity and at least one polymerase containing 3'→5' exonuclease activity.

2. The method of claim 1, wherein the at least one polymerase lacking 3'→5' exonuclease activity is selected from the group Tth, Taq, and Tfl.

3. The method of claim 1, wherein the at least one polymerase containing 3'→5' exonuclease activity is selected from the group Pfu, Plo, and Pwo.

4. The method of claim 1, wherein the at least one polymerase lacking 3'→5' exonuclease activity is present in a concentration of from about 0.125U to about 4U per 25 µl reaction.

5. The method of claim 1, wherein the at least one polymerase lacking 3'→5' exonuclease activity is present in a concentration of 4U per 25 µl reaction.

6. The method of claim 1, wherein the at least one polymerase containing 3'→5' exonuclease activity is present in a concentration of from about 0.0125U to about 0.4U per 25 µl reaction.

7. The method of claim 1, wherein the at least one polymerase containing 3'→5' exonuclease activity is present in a concentration of 0.1U per 25 µl reaction.

8. The method of claim 1, wherein the at least one polymerase lacking 3'→5' exonuclease activity and the at least one polymerase containing 3'→5' exonuclease activity are present in a ratio of from about 1:0.0125 to about 1:0.2.

9. The method of claim 1, wherein the at least one polymerase lacking 3'→5' exonuclease activity and the at least one polymerase containing 3'→5' exonuclease activity are present in a ratio of 1:0.05.

10. The method of claim 1, wherein the at least one polymerase lacking 3'→5' exonuclease activity and the at least one polymerase containing 3'→5' exonuclease activity are present in a ratio of 1:0.1.

11. The method of claim 1, wherein the DNA segments are amplified using a first primer having a 3' portion which is complementary to the 3' end of the antisense strand of the DNA segment and a 5' tail which is complementary to the 5' end of the second primer for the previous DNA segment; and a second primer having a 3' portion which is complementary to the 3' end of the sense strand of the DNA segment and a 5' tail which is complementary to the 5' end of the first primer for the subsequent segment.

12. The method of claim 1, wherein the DNA segments are amplified using a first primer having a 3' portion which is complementary to the 3' end of the antisense strand of the DNA segment and a 5' tail which is complementary to a sequence internal to the previous DNA segment; and a second primer having a 3' portion which is complementary to the 3' end of the sense strand of the DNA segment and a 5' tail which is complementary to a sequence internal to the subsequent segment.

13. The method of claim 1, wherein the DNA segments are exons of a single gene.

14. The method of claim 1, wherein the DNA segments are exons of different genes.

15. The method of claim 1, wherein the DNA segments are nonexon portions of a single gene.

16. The method of claim 1, wherein the DNA segments are nonexon portions of different genes.

17. The method of claim 1, wherein the DNA segments originate from organisms of the same species.

18. The method of claim 1, wherein the DNA segments originate from organisms of one or more different species.

19. The method of claim 1, wherein the DNA segments contain tails which are complementary to the tails of adjacent DNA segments.

20. A method of producing and amplifying DNA containing at least three linked DNA segments which occur in non-adjacent portions of target DNA, comprising
   a. providing a first primer and a second primer for each DNA segment to be amplified,
      i. the first primer (termed the D primer) having a 3' portion which is complementary to the 3' end of the antisense strand of the DNA segment and a 5' tail which is complementary to the 5' end of the second primer for the previous DNA segment;
      ii. the second primer (termed the U primer) having a 3' portion which is complementary to the 3' end of the sense strand of the DNA segment and a 5' tail which is complementary to the 5' end of the first primer for the subsequent segment;
   b. amplifying the at least three DNA segments by multiplex PCR using the pairs of first and second primers; and
   c. subjecting the at least three amplified DNA segments to a linking PCR using a first primer which is complementary to the antisense strand of the first DNA segment to be linked, a second primer which is complementary to the sense strand of the last DNA segment to be linked, at least one polymerase lacking 3'→5' exonuclease activity and at least one polymerase containing 3'→5' exonuclease activity.

21. A method of producing and amplifying DNA containing at least three linked DNA segments which occur in non-adjacent portions of target DNA, comprising
   a. providing a first primer and a second primer for each DNA segment to be amplified,
      i. the first primer (termed the D primer) having a 3' portion which is complementary to the 3' end of the antisense strand of the DNA segment and a 5' tail which is complementary to a sequence internal to the previous DNA segment;
      ii. the second primer (termed the U primer) having a 3' portion which is complementary to the 3' end of the sense strand of the DNA segment and a 5' tail which is complementary to a sequence internal to the subsequent segment;
   b. amplifying the at least three DNA segments by multiplex PCR using the pairs of first and second primers; and
   c. subjecting the at least three amplified DNA segments to a linking PCR using a first primer which is complementary to the antisense strand of the first DNA segment to be linked, a second primer which is complementary to the sense strand of the last DNA segment to be linked, at least one polymerase lacking 3'→5' exonuclease activity and at least one polymerase containing 3'→5' exonuclease activity.

22. The method of claim 20, wherein after step b and before step c unincorporated primers are removed from the amplification reaction mixture.

23. The method of claim 21, wherein after step b and before step c unincorporated primers are removed from the amplification reaction mixture.

24. The method of claim 20, wherein the 5' tails do not overlap the 3' portion which is complementary to the 3' end of the sense strand of the DNA segment.

25. The method of claim 20, wherein the 5' tails overlap the 3' portion which is complementary to the 3' end of the sense strand of the DNA segment.

26. The method of claim 20, wherein the 5' tails overlap the 3' portion which is complementary to the 3' end of the sense strand of the DNA segment by four nucleotides.

27. The method of claim 20, wherein the 5' tails are GC-rich.

28. The method of claim 20, wherein the 5' tails contain about 60% to about 70% G and C nucleotides.

29. The method of claim 20, wherein the 5' tails are about 10 to about 15 nucleotides long.

30. The method of claim 21, wherein the 5' tails are about 10 to about 15 nucleotides long.

31. The method of claim 20, wherein the 5' tails are 12 nucleotides long.

32. The method of claim 21, wherein the 5' tails are 12 nucleotides long.

33. The method of claim 20, wherein the DNA segments are exons.

34. The method of claim 21, wherein the DNA segments are exons.

35. The method of claim 20, wherein the DNA segments are exons of a single gene.

36. The method of claim 21, wherein the DNA segments are exons of a single gene.

37. The method of claim 20, wherein the DNA segments are exons of different genes.

38. The method of claim 21, wherein the DNA segments are exons of different genes.

39. The method of claim 20, wherein the DNA segments are nonexon portions of a single gene.

40. The method of claim 21, wherein the DNA segments are nonexon portions of a single gene.

41. The method of claim 20, wherein the DNA segments are nonexon portions of different genes.

42. The method of claim 21, wherein the DNA segments are nonexon portions of different genes.

43. The method of claim 20, wherein the DNA segments originate from organisms of the same species.

44. The method of claim 21, wherein the DNA segments originate from organisms of the same species.

45. The method of claim 20, wherein the DNA segments originate from organisms of one or more different species.

46. The method of claim 21, wherein the DNA segments originate from organisms of one or more different species.

47. The method of claim 20, wherein the linked DNA product is a copy of a gene lacking large introns.

48. The method of claim 21, wherein the linked DNA product is a copy of a gene lacking large introns.

49. The method of claim 20, wherein the linked DNA product contains a mutation.

50. The method of claim 21, wherein the linked DNA product contains a mutation.

51. The method of claim 20, wherein the linking polymerase chain reaction mixture contains a solid or liquid macromolecular additive.

52. The method of claim 21, wherein the linking polymerase chain reaction mixture contains a solid or liquid macromolecular additive.

53. The method of claim 51, wherein the macromolecular additive is polyethylene glycol.

54. The method of claim 52, wherein the macromolecular additive is polyethylene glycol.

* * * * *

SEQUENCE LISTING

<160> NUMBER OF SEQ ID NOS: 24

<210> SEQ ID NO 1
<211> LENGTH: 28
<212> TYPE: DNA
<213> ORGANISM: Homo sapiens

<400> SEQUENCE: 1
gttcgcagag ggtttgtgcc aggagcct                28

<210> SEQ ID NO 2
<211> LENGTH: 29
<212> TYPE: DNA
<213> ORGANISM: Homo sapiens

```
<400> SEQUENCE: 2
aggacgaccg ctagcccgtg actcagaga                                         29

<210> SEQ ID NO 3
<211> LENGTH: 30
<212> TYPE: DNA
<213> ORGANISM: Homo sapiens

<400> SEQUENCE: 3
agcggtcgtc ctccagggtt ggaagtgtct                                        30

<210> SEQ ID NO 4
<211> LENGTH: 30
<212> TYPE: DNA
<213> ORGANISM: Homo sapiens

<400> SEQUENCE: 4
cgatggcaca gcgatacggc caggcattga                                        30

<210> SEQ ID NO 5
<211> LENGTH: 31
<212> TYPE: DNA
<213> ORGANISM: Homo sapiens

<400> SEQUENCE: 5
gctgtgccat cgtccgtcat aaagtcaaac a                                      31

<210> SEQ ID NO 6
<211> LENGTH: 31
<212> TYPE: DNA
<213> ORGANISM: Homo sapiens

<400> SEQUENCE: 6
gaggtgggtg tccctatggc tttccaacct a                                      31

<210> SEQ ID NO 7
<211> LENGTH: 31
<212> TYPE: DNA
<213> ORGANISM: Homo sapiens

<400> SEQUENCE: 7
gacacccacc tcaccctctc actcatgtga t                                      31

<210> SEQ ID NO 8
<211> LENGTH: 29
<212> TYPE: DNA
<213> ORGANISM: Homo sapiens

<400> SEQUENCE: 8
cccgtgagga cagacccaaa acccaaaat                                         29

<210> SEQ ID NO 9
<211> LENGTH: 28
<212> TYPE: DNA
<213> ORGANISM: Homo sapiens

<400> SEQUENCE: 9
caacgggtca ggaggggttg atgggatt                                          28

<210> SEQ ID NO 10
<211> LENGTH: 29
<212> TYPE: DNA
```

```
<213> ORGANISM: Homo sapiens

<400> SEQUENCE: 10
cgtgtgggtg ctgagggagg ctgtcagtg                              29

<210> SEQ ID NO 11
<211> LENGTH: 24
<212> TYPE: DNA
<213> ORGANISM: Homo sapiens

<400> SEQUENCE: 11
tcgcagagga ggccattgga aata                                   24

<210> SEQ ID NO 12
<211> LENGTH: 25
<212> TYPE: DNA
<213> ORGANISM: Homo sapiens

<400> SEQUENCE: 12
gtaagcggtc gtgctggctg ttaga                                  25

<210> SEQ ID NO 13
<211> LENGTH: 29
<212> TYPE: DNA
<213> ORGANISM: Homo sapiens

<400> SEQUENCE: 13
cacgaccgct tactggaatt ctcttgact                              29

<210> SEQ ID NO 14
<211> LENGTH: 27
<212> TYPE: DNA
<213> ORGANISM: Homo sapiens

<400> SEQUENCE: 14
gccaacagtg gcataaccct gtagtat                                27

<210> SEQ ID NO 15
<211> LENGTH: 25
<212> TYPE: DNA
<213> ORGANISM: Homo sapiens

<400> SEQUENCE: 15
gccactgttg gcttccaggt cagta                                  25

<210> SEQ ID NO 16
<211> LENGTH: 28
<212> TYPE: DNA
<213> ORGANISM: Homo sapiens

<400> SEQUENCE: 16
ggtccgggat caaaggtatg tttttaag                               28

<210> SEQ ID NO 17
<211> LENGTH: 27
<212> TYPE: DNA
<213> ORGANISM: Homo sapiens

<400> SEQUENCE: 17
tgatcccgga cccatacatg agtcagt                                27

<210> SEQ ID NO 18
<211> LENGTH: 27
```

```
<212> TYPE: DNA
<213> ORGANISM: Homo sapiens

<400> SEQUENCE: 18
acggagacag gaagcagatt caagtag                                          27

<210> SEQ ID NO 19
<211> LENGTH: 23
<212> TYPE: DNA
<213> ORGANISM: Homo sapiens

<400> SEQUENCE: 19
tcaaggagga gggagatgga cat                                              23

<210> SEQ ID NO 20
<211> LENGTH: 23
<212> TYPE: DNA
<213> ORGANISM: Homo sapiens

<400> SEQUENCE: 20
tggtgtgctt aaaatgctga agt                                              23

<210> SEQ ID NO 21
<211> LENGTH: 31
<212> TYPE: DNA
<213> ORGANISM: Homo sapiens

<400> SEQUENCE: 21
gctgtgccat cgtccgtcat aaagtcaaac a                                     31

<210> SEQ ID NO 22
<211> LENGTH: 29
<212> TYPE: DNA
<213> ORGANISM: Homo sapiens

<400> SEQUENCE: 22
cgatggcaca gcgatacgcc aggcattga                                        29

<210> SEQ ID NO 23
<211> LENGTH: 25
<212> TYPE: DNA
<213> ORGANISM: Homo sapiens

<400> SEQUENCE: 23
gccactgttg gcttccaggt cagta                                            25

<210> SEQ ID NO 24
<211> LENGTH: 27
<212> TYPE: DNA
<213> ORGANISM: Homo sapiens

<400> SEQUENCE: 24
gccaacagtg gcataaccct gtagtat                                          27
```